United States Patent
Taylor et al.

[19]

[11] Patent Number: 6,152,146

[45] Date of Patent: *Nov. 28, 2000

[54] ION EMITTING GROOMING BRUSH

[75] Inventors: Charles E. Taylor, Sebastopol; Shek Fai Lau, Foster City, both of Calif.

[73] Assignee: Sharper Image Corporation, San Francisco, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/344,516

[22] Filed: Jun. 25, 1999

Related U.S. Application Data

[63] Continuation of application No. 09/163,024, Sep. 29, 1998, Pat. No. 5,975,090.

[51] Int. Cl.$^7$ .................................................. A45D 19/16
[52] U.S. Cl. ...................... 132/116; 132/154; 132/272; 607/79
[58] Field of Search .................................... 132/112, 116, 132/148, 152, 154, 271, 272; 607/79

[56] References Cited

U.S. PATENT DOCUMENTS

| | | | |
|---|---|---|---|
| 2,590,447 | 3/1952 | Nord, Jr. et al. | 607/79 |
| 4,632,135 | 12/1986 | Lenting et al. | 132/313 |
| 4,789,801 | 12/1988 | Lee . | |
| 5,072,746 | 12/1991 | Kantor | 132/161 |
| 5,386,839 | 2/1995 | Chen | 132/152 |
| 5,569,368 | 10/1996 | Larsky et al. | 132/148 |
| 5,921,251 | 7/1999 | Joshi | 123/112 |

OTHER PUBLICATIONS

"Zenion Elf Device" drawing.
Electrical Schematic and promotional material available from Zenion Industries, 7 p. (possibly published prior to Jan. 1998).
Promotional material available from Zenion Industries for the Plasma–Pure 100/200/300, 2 p. (possibly published prior to Jan. 1998).
Promotional material available from Zenion Industries for the Plasma–Tron, 2 p. (possibly published prior to Jan. 1998).

*Primary Examiner*—Todd E. Manahan
*Attorney, Agent, or Firm*—Flehr Hohbach Test Albritton & Herbert LLP

[57] ABSTRACT

A hair brush includes a self-contained ion generator that subjects the hair and scalp being brushed to an outflow of ionized air containing safe amounts of ozone. The ion generator includes a high voltage pulse generator whose output pulses are coupled between first and second electrode arrays. Preferably the first array comprises at least one metal pin spaced coaxially-apart from a metal ring-like structure. Alternatively, the first array may comprise one or more wire electrodes spaced staggeringly apart from a second array comprising hollow "U"-shaped electrodes. Preferably a ratio between effective area of an electrode in the second array compared to effective area of an electrode in the first array exceeds about 15:1 and preferably is about 20:1. An electric field produced by the high voltage pulses between the arrays produces an electrostatic flow of ionized air containing safe amounts of ozone. The outflow of ionized air and ozone is directed between the brush bristles onto the hair and scalp being groomed.

32 Claims, 13 Drawing Sheets

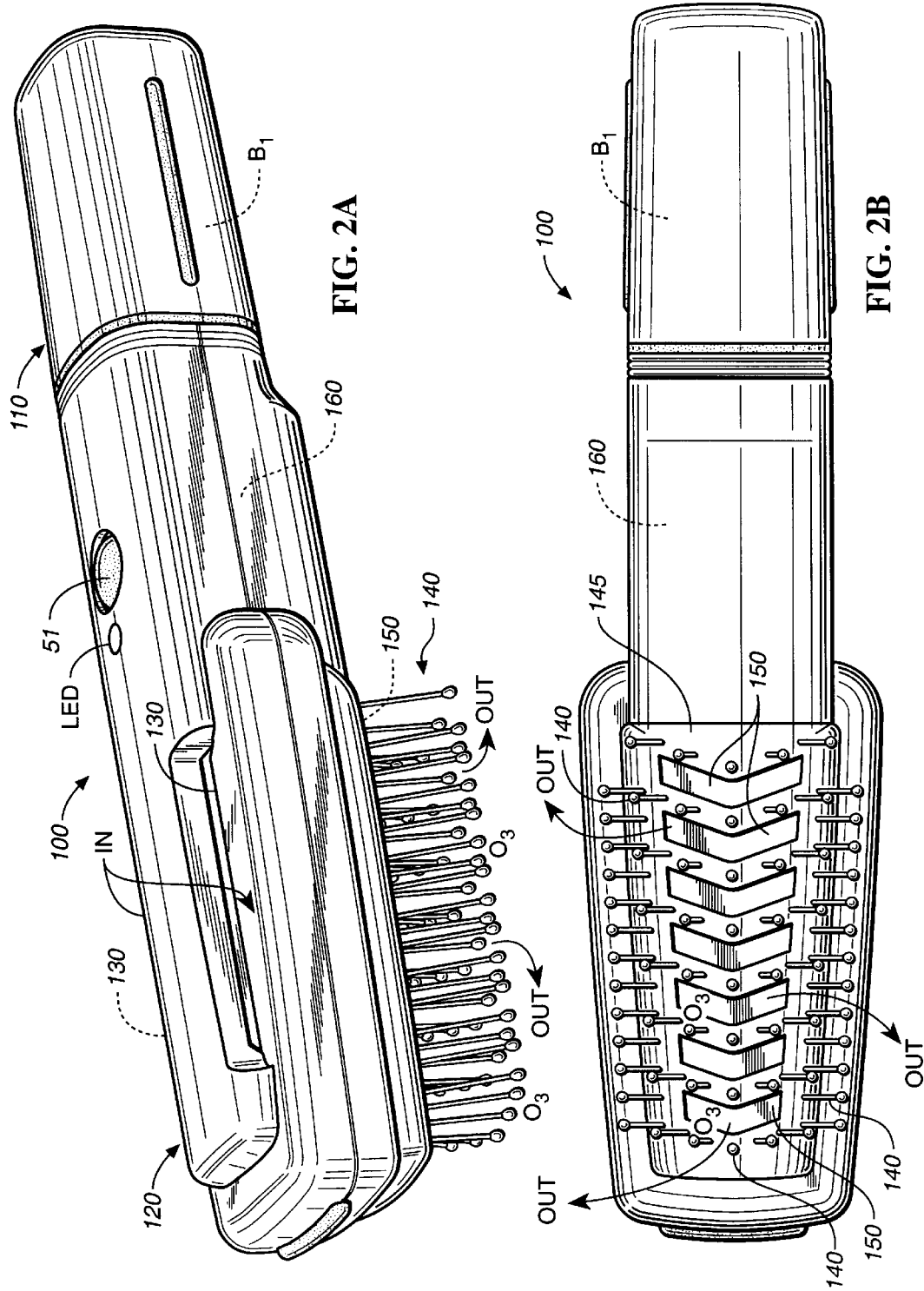

ION EMITTING GROOMING BRUSH

This is a continuation of application Ser. No. 09/163,024 filed Sep. 29, 1998 now U.S. Pat. No. 5,975,090.

FIELD OF THE INVENTION

This invention relates to grooming products such as hair brushes for humans and pets, and more specifically to hair brushes that promote grooming by emitting ionized air directed to the hairs being brushed.

BACKGROUND OF THE INVENTION

Hair brushes have been used for thousands of years in an attempt to groom hair. In the grooming process, bristles projecting from a hair brush are forced toward the scalp in an attempt to cause individual hairs to either fall into place, or to align with each other somewhat.

However common experience indicates that conventional hair brushing is not always successful. For example, individual hairs frequently refuse to closely align closely with each other. One explanation may be that scales on the individual hair shafts can project outward, which prevents adjacent hairs from being forced into close alignment; the projecting scales simply get in the way.

While hair brushing can be stimulating to the scalp, brushing per se does not always achieve a well groomed appearance, and accomplishes little or nothing with respect to cleaning or conditioning the hair. While sufficiently large foreign particles, e.g., dirt, dandruff, may be brushed out of the hair, smaller particles can remain in place on the hair shafts or hair scales. Brushing one's hair truly does not provide conditioning in that after brushing the hair frequently as it was before, give or take some mechanical repositioning of the hairs.

It is known in the art to produce an air flow electro-kinetically by directly converting electrical power into a flow of air without mechanically moving components. One such system is described in U.S. Pat. No. 4,789,801 to Lee (1988), depicted herein in simplified form as FIGS. 1A and 1B. Lee's system 10 provides a first array of small area ("minisectional") electrodes 20 is spaced-apart symmetrically from a second array of larger area ("maxisectional") electrodes 30, with a high voltage (e.g., 5 KV) pulse generator 40 coupled between the two arrays. Generator 40 outputs high voltage pulses that ionize the air between the arrays, producing an air flow 50 from the minisectional array toward the maxisectional array results. The high voltage field present between the two arrays can release ozone ($O_3$), which can advantageously safely destroy many types of bacteria if excessive quantities of ozone are not released.

Unfortunately, Lee's tear-shaped maxisectional electrodes are relatively expensive to fabricate, most likely requiring mold-casting or extrusion processes. Further, air float and ion generation efficiency is not especially high using Lee's configuration.

There is a need for a hair brush that can not only brush hair, but provide a measure of cleaning and/or conditioning as well. Preferably such hair brush should subject the hair being brushed to an ion flow to promote cleaning and grooming.

The present invention provides such a grooming brush.

SUMMARY OF THE PRESENT INVENTION

The present invention provides a hair brush whose body includes a handle portion and a head portion defining at least one vent and including projecting bristles. More preferably, the head portion upperside will define at least one air intake vent and the head portion underside defines at least one ionized air outlet vent.

Contained within the hair brush body is a battery-operated ionizer unit with DC battery power supply. The ionizer unit includes a DC:DC inverter that boosts the battery voltage to high voltage, and a pulse generator that receives the high voltage DC and outputs high voltage pulses of perhaps 10 KV peak-to-peak, although high voltage DC could be used instead of pulses. The unit also includes an electrode assembly unit comprising first and second spaced-apart arrays of conducting electrodes, the first array and second array being coupled, respectively, preferably to the positive and negative output ports of the high voltage pulse generator.

The electrode assembly preferably is formed using first and second arrays of readily manufacturable electrode types. In one embodiment, the first array comprises wire-like electrodes and the second array comprises "U"-shaped electrodes having one or two trailing surfaces. In an even more efficient embodiment, the first array includes at least one pin or cone-like electrode and the second array is an annular washer-like electrode. The electrode assembly may comprise various combinations of the described first and second array electrodes. In the various embodiments, the ratio between effective area of the second array electrodes to the first array electrodes is at least about 20:1.

The high voltage pulses create an electric field between the first and second electrode arrays. This field produces an electro-kinetic airflow going from the first array toward the second array, the airflow being rich in ions and in ozone ($O_3$). Ambient air enters the hair brush head via air intake vent(s), and ionized air (with ozone) exits the hair brush through outlet vent(s) in the bristle portion of the head. However, in practice if only one vent is present, it suffices as both an intake and an outlet vent. Preferably a visual indicator is coupled to the ionizer unit to visually confirm to a user when the unit is ready for ionizing operation, and when ionization is actually occurring.

Hair brushed with the bristles is subjected to a gentle flow of ionized air from the outlet vent(s). The hair seems to fall more rapidly into place with a cleaner and more conditioned appearance, compared to hair groomed with an ordinary hair brush. The ozone emissions can kill many types of germs and bacteria that may be present on the hair and scalp and can deodorize the hair and scalp.

Other features and advantages of the invention will appear from the following description in which the preferred embodiments have been set forth in detail, in conjunction with the accompanying drawings.

BRIEF DESCRIPTION OF THE DRAWINGS

FIG. 2A is an perspective view of a preferred embodiment of an ionizing hair brush, according to the present invention;

FIG. 2B is a bottom view of a preferred embodiment of an ionizing hair brush, according to the present invention;

DETAILED DESCRIPTION OF THE PREFERRED EMBODIMENT

Figure 1A:
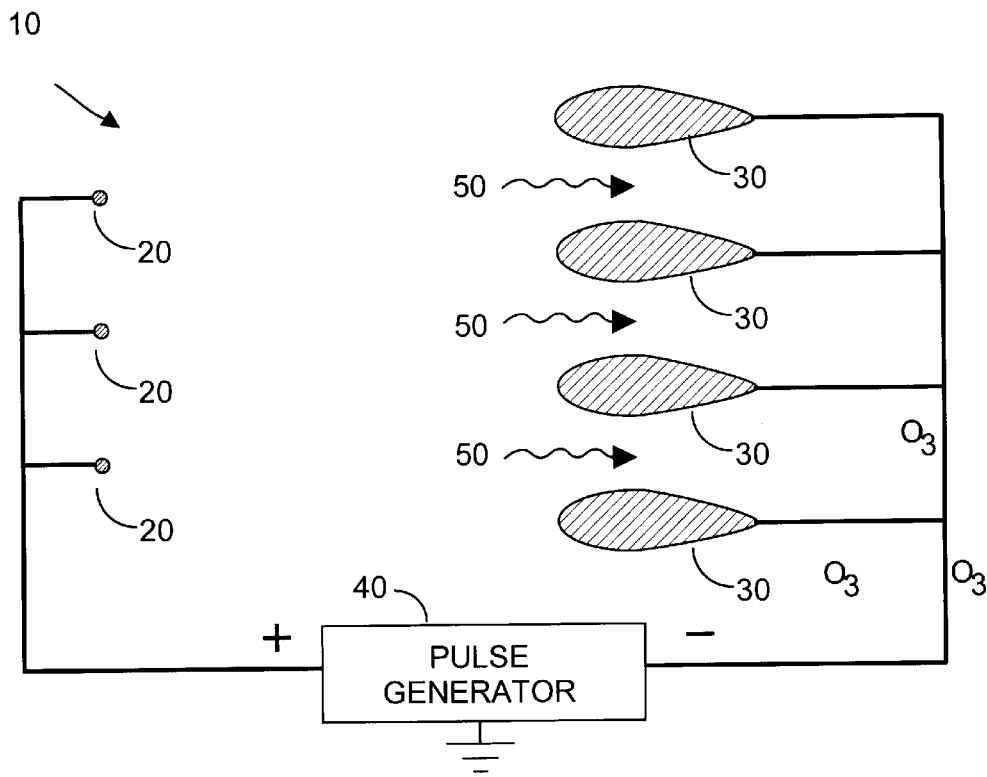
FIG. 1A and 1B are depictions of Lee-type electrostatic generators, according to the prior art.
Figure 1B:
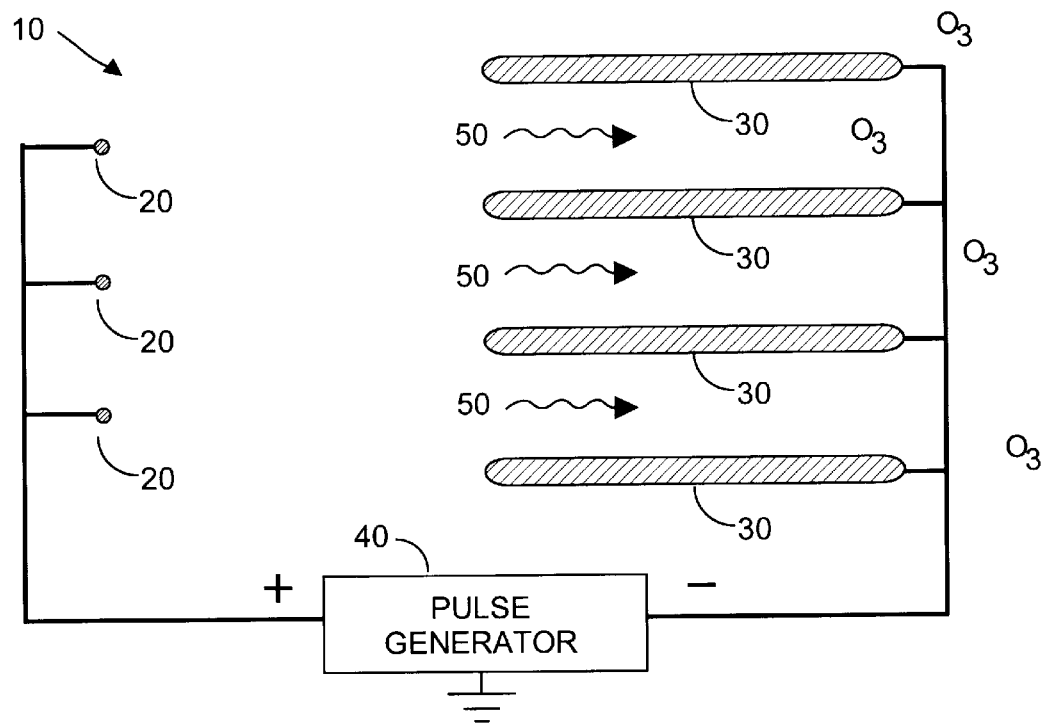

FIGS. 2A and 2B depict an ionized hair brush 100 according to the present invention as having a body that includes a handle portion 110 and a head portion 120. Head portion 120 includes one or more air intake vents 130, brush bristles 140 that protrude from a brush plate 145 attached to the brushing surface of the hair brush, and one or more outlet vents 150. Internal to the hair brush body is an ion generating unit 160, powered by a battery B1 (preferably at least 6 VDC) contained within the hair brush and energizable via a switch S1, preferably mounted on the hair brush 100. As such, ion generating unit 160 is self-contained in that other than ambient air, nothing is required from beyond the body of the hair brush for operation of the present invention. Of course if desired, a DC power supply could be disposed external to the hair brush body, and power brought into the hair brush via a cable.

Preferably handle portion 110 is detachable from head portion 120, to provide access to battery B1, preferably five NiCd rechargeable cells or four disposable cells. The housing material is preferably inexpensive, lightweight, and easy to fabricate, ABS plastic for example. Hair brush 100 is preferably approximately the size of typical hair brushes, for example an overall length of perhaps 235 mm, and a maximum width of perhaps 58 mm, although other dimensions can of course be used.

Brush plate 145 may be removably attached to hair brush 100, for ease of cleaning the bristles, for providing access to an ion-emitting electrode assembly within the brush head, as well as for inserting a different brush plate bearing a different type of bristles. Thus, for reasons of hygiene different family members might use the same hair brush 100, but with different sets of bristles that are interchangeable via different brush plates 145. Alternatively, different types or shapes or configurations of bristles might be used interchangeably simply by inserting different brush plate-bristle assemblies into the head portion of the present invention.

It will also be appreciated that use of the present invention is not limited to grooming humans, and one could use the present invention to groom animals including household pets (e.g., dogs, cats). Thus, whereas bristles 140 might be fabricated from nylon or plastic for grooming human hair, the bristles might instead be metal when the hair brush is used to groom animal fur. Thus, if desired, a brush plate 145 containing nylon bristles could be replaced with a different brush plate containing metal bristles for grooming the family cat.

The ability to remove brush plate 145 also provides ready access to electrodes within the brush head, for purposes of cleaning and, if necessary, replacement. It is to be understood that although FIGS. 2A and 2B depict an exemplary embodiment for hair brush 100, other configurations may be used. Different configurations of inlet vent(s) 130 and/or outlet vent(s) 150 may be used. Thus, more or fewer such vents may be provided, the locations location and/or shapes of which may differ from what is depicted in FIGS. 2A and 2B. The purpose of vents 130 and 150 is to ensure that an adequate flow of ambient air may be drawn into or made available to unit 130, and that an adequate flow of ionized air that includes safe amounts of $O_3$ flows out from unit 130 towards the grooming area.

Figure 3:
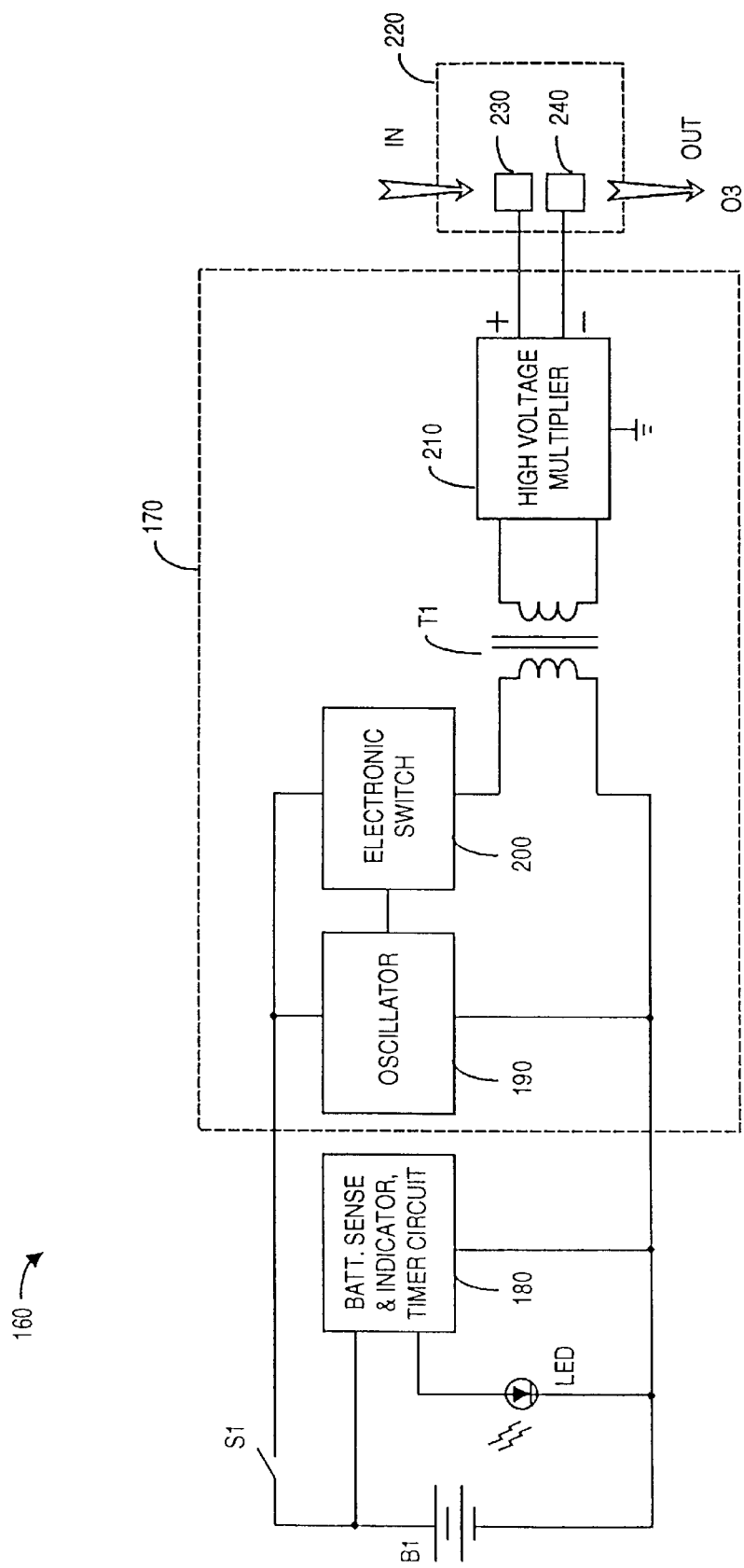
FIG. 3 is an electrical block diagram of the present invention.

As best seen in FIG. 3, ion generating unit 160 includes a high voltage pulse generator unit 170 and optionally an indicator circuit 180. Circuit 180 senses potential on battery B1 and indicates whether battery potential is sufficient to generate ions and when ion generation is occurring. In the preferred embodiment, a visual indicator is used, preferably a two-color light emitting diode ("LED"). Of course other indicator devices may be used, including for example, blinking indicator(s), and/or audible indicator(s). optionally, circuit 180 includes timing components that will turn-off generation of ions and ozone after a predetermined time, for example two minutes. Such a turn-off feature will preserve battery lifetime in the event S1 is other than a push-to-maintain contact type switch. Thus, a user who pushes S1, combs his or her hair (or grooms a pet), and forgets to turn-off S1 will not necessarily deplete battery B1, as circuitry 180 will turn-off the present invention for the user.

As shown in FIG. 3, high voltage pulse generator unit 170 preferably comprises a low voltage oscillator circuit 190 of perhaps 20 KHz frequency, that outputs low voltage pulses to an electronic switch 200, e.g., a thyristor or the like. Switch 200 switchably couples the low voltage pulses to the input winding of a step-up transformer T1. The secondary winding of T1 is coupled to a high voltage multiplier circuit 210 that outputs high voltage pulses. Preferably the circuitry and components comprising high voltage pulse generator 170 and sense/indicator circuit (and timing circuit) 180 are fabricated on a printed circuit board that is mounted within head portion 120 of hair brush 100.

Output pulses from high voltage generator 170 preferably are at least 10 KV peak-to-peak with an effective DC offset of perhaps half the peak-to-peak voltage, and have a frequency of perhaps 20 KHz. The pulse train output preferably has a duty cycle of perhaps 10%, which will promote battery lifetime. Of course, different peak-peak amplitudes, DC offsets, pulse train waveshapes, duty cycle, and/or repetition frequencies may instead be used. Indeed, a 100% pulse train (e.g., an essentially DC high voltage) may be used, albeit with shorter battery lifetime.

Frequency of oscillation is not especially critical but frequency of at least about 20 KHz is preferred as being inaudible to humans. However if brush 100 is intended for use in grooming pets, even higher operating frequency may be desired such that the present invention does not emit audible sounds that would disturb an animal being groomed with the brush.

The output from high voltage pulse generator unit 170 is coupled to an electrode assembly 220 that comprises a first electrode array 230 and a second electrode array 240. Unit 170 functions as a DC:DC high voltage generator, and could be implemented using other circuitry and/or techniques to output high voltage pulses that are input to electrode assembly 220.

In the embodiment of FIG. 3, the positive output terminal of unit 170 is coupled to first electrode array 230, and the negative output terminal is coupled to second electrode array 240. This coupling polarity has been found to work well. An electrostatic flow of air is created, going from the first electrode array towards the second electrode array. (This flow is denoted "OUT" in the figures.) Accordingly electrode assembly 220 is mounted in the head portion 120 of hair brush 100 such that second electrode array 240 is closer to the brushing surface (e.g., bristle-containing region where outlet vent(s) 150 are located) than is first electrode array 230.

When voltage or pulses from high voltage pulse generator 170 are coupled across first and second electrode arrays 230 and 240, it is believed that a plasma-like field is created surrounding electrodes 232 in first array 230. This electric field ionizes the air between the first and second electrode arrays and establishes an "OUT" airflow that moves towards the second array. It is understood that the IN flow enters brush 100 via vent(s) 130, and that the OUT flow exits brush 100 via vent(s) 150.

It is believed that ozone and ions are generated simultaneously by the first array electrode(s) 232, essentially as a function of the potential from generator 170 coupled to the first array. Ozone generation may be increased or decreased by increasing or decreasing the potential at the first array. Coupling an opposite polarity potential to the second array electrode(s) 242 essentially accelerates the motion of ions generated at the first array, producing the air flow denoted as "OUT" in the figures. As the ions move toward the second array, it is believed that they push or move air molecules toward the second array. The relative velocity of this motion may be increased by decreasing the potential at the second array relative to the potential at the first array.

For example, if +10 KV were applied to the first array electrode(s), and no potential were applied to the second array electrode(s), a cloud of ions (whose net charge is positive) would form adjacent the first electrode array. Further, the relatively high 10 KV potential would generate substantial ozone. By coupling a relatively negative potential to the second array electrode(s), the velocity of the air mass moved by the net emitted ions increases, as momentum of the moving ions is conserved.

On the other hand, if it were desired to maintain the same effective outflow (OUT) velocity but to generate less ozone, the exemplary 10 KV potential could be divided between the electrode arrays. For example, generator 170 could provide +6 KV (or some other fraction) to the first array electrode(s) and −4 KV (or some other fraction) to the second array electrode(s). In this example, it is understood that the +6 KV and the −4 KV are measured relative to ground. Understandable it is desired that the present invention operate to output safe amounts of ozone.

As noted, outflow (OUT) preferably includes safe amounts of $O_3$ that can destroy or at least substantially alter bacteria, germs, and other living (or quasi-living) matter subjected to the outflow. Thus, when switch S1 is closed and B1 has sufficient operating potential, pulses from high voltage pulse generator unit 170 create an outflow (OUT) of ionized air and $O_3$. When S1 is closed, LED will first visually signal whether sufficient B1 potential is present, and if present, then signal when ionization is occurring. If LED fails to indicate sufficient operating voltage, the user will know to replace B1 or, if rechargeable cells are used, to recharge B1. For example, if visual indicator is a two-color device, the LED could signal red when B1 potential exceeds a minimum threshold, e.g., 5.5 VDC. Further, LED could then signal green when S1 is depressed and unit 160 is actually outputting ionized air. If the battery potential is too low, the LED will not light, which advises the user to replace or re-charge battery source B1.

Preferably operating parameters of the present invention are set during manufacture and are not user-adjustable. For example, increasing the peak-to-peak output voltage and/or duty cycle in the high voltage pulses generated by unit 170 can increase air flowrate, ion content, and ozone content. In the preferred embodiment, output flowrate is about 90 feet/minute, ion content is about 2,000,000/cc and ozone content is about 50 ppb (over ambient) to perhaps 2,000 ppb (over ambient). Decreasing the R2/R1 ratio below about 20:1 will decrease flow rate, as will decreasing the peak-to-peak voltage and/or duty cycle of the high voltage pulses coupled between the first and second electrode arrays.

In practice, a user holds and uses hair brush 100 in conventional fashion to brush hair. With S1 energized, ionization unit 160 emits ionized air and preferably some ozone ($O_3$) via outlet vents 150. The hair being groomed advantageously is subjected to this outflow ("OUT") of air and ozone. Beneficially, the brushed air seems to align together more coherently than when using a non-ionized brush. The explanation possibly is that electrically charged ions in the outflow cause scales on individual hair shafts to lie more closely against the shaft, rather than project outwardly to prevent adjacent hairs from closely aligning. In general, the hair will appear more groomed.

Odors in the hair and scalp being brushed will diminish, and some types of germs or bacteria, if present, can be killed by the outflow from hair brush 100. In short, not only is the hair brushed and groomed more effectively than with a passive prior art brush, e.g., a brush that does not actively emit ions, but hygiene is promoted as well.

Having described various aspects of the invention in general, preferred embodiments of electrode assembly 220 will now be described. In the various embodiments, electrode assembly 220 will comprise a first array 230 of at least one electrode 232, and will further comprise a second array 240 of preferably at least one electrode 242. Understandably material(s) for electrodes 232 and 242 should conduct electricity, be resilient to corrosive effects from the application of high voltage, yet be strong enough to be cleaned.

In the various electrode assemblies to be described herein, electrode(s) 232 in the first electrode array 230 are preferably fabricated from tungsten. Tungsten is sufficiently robust to withstand cleaning, has a high melting point to retard breakdown due to ionization, and has a rough exterior surface that seems to promote efficient ionization. On the other hand, electrodes 242 preferably will have a highly polished exterior surface to minimize unwanted point-to-point radiation. As such, electrodes 242 preferably are fabricated from stainless steel, brass, among other materials. The polished surface of electrodes 232 also promotes ease of electrode cleaning.

In contrast to the prior art electrodes disclosed by Lee, electrodes 232 and 242 according to the present invention are light weight, easy to fabricate, and lend themselves to mass production. Further, electrodes 232 and 242 described herein promote more efficient generation of ionized air, and production of safe amounts of ozone, $O_3$.

In the present invention, a high voltage pulse generator 170 is coupled between the first electrode array 230 and the second electrode array 240. The high voltage pulses produce a flow of ionized air that travels in the direction from the first array towards the second array (indicated herein by hollow arrows denoted "OUT"). As such, electrode(s) 232 may be referred to as an emitting electrode, and electrodes 242 may be referred to as collector electrodes. This outflow advantageously contains safe amounts of $O_3$, and exits the present invention from vent(s) 150, as shown in FIGS. 2A and 2B. Although a generator of high voltage pulses is preferred and will promote battery life, in practice high voltage DC (e.g., pulses having 100% duty cycle) may instead be used.

According to the present invention, it is preferred that the positive output terminal or port of the high voltage pulse generator be coupled to electrodes 232, and that the negative output terminal or port be coupled to electrodes 242. It is believed that the net polarity of the emitted ions is positive, e.g., more positive ions than negative ions are emitted. In any event, the preferred electrode assembly electrical coupling minimizes audible hum from electrodes 232 contrasted with reverse polarity (e.g., interchanging the positive and negative output port connections). Further, the preferred electrical coupling seems to produce ions that help keep hair in place, as opposed to putting a static charge into the hair that can produce an undesired "flyaway" hair appearance. In some embodiments, however, one port (preferably the negative port) of high voltage pulse generator may in fact be the ambient air. Thus, electrodes in the second array need not be connected to the high voltage pulse generator using wire. Nonetheless, there will be an "effective connection" between the second array electrodes and one output port of the high voltage pulse generator, in this instance, via ambient air.

Figure 4A:
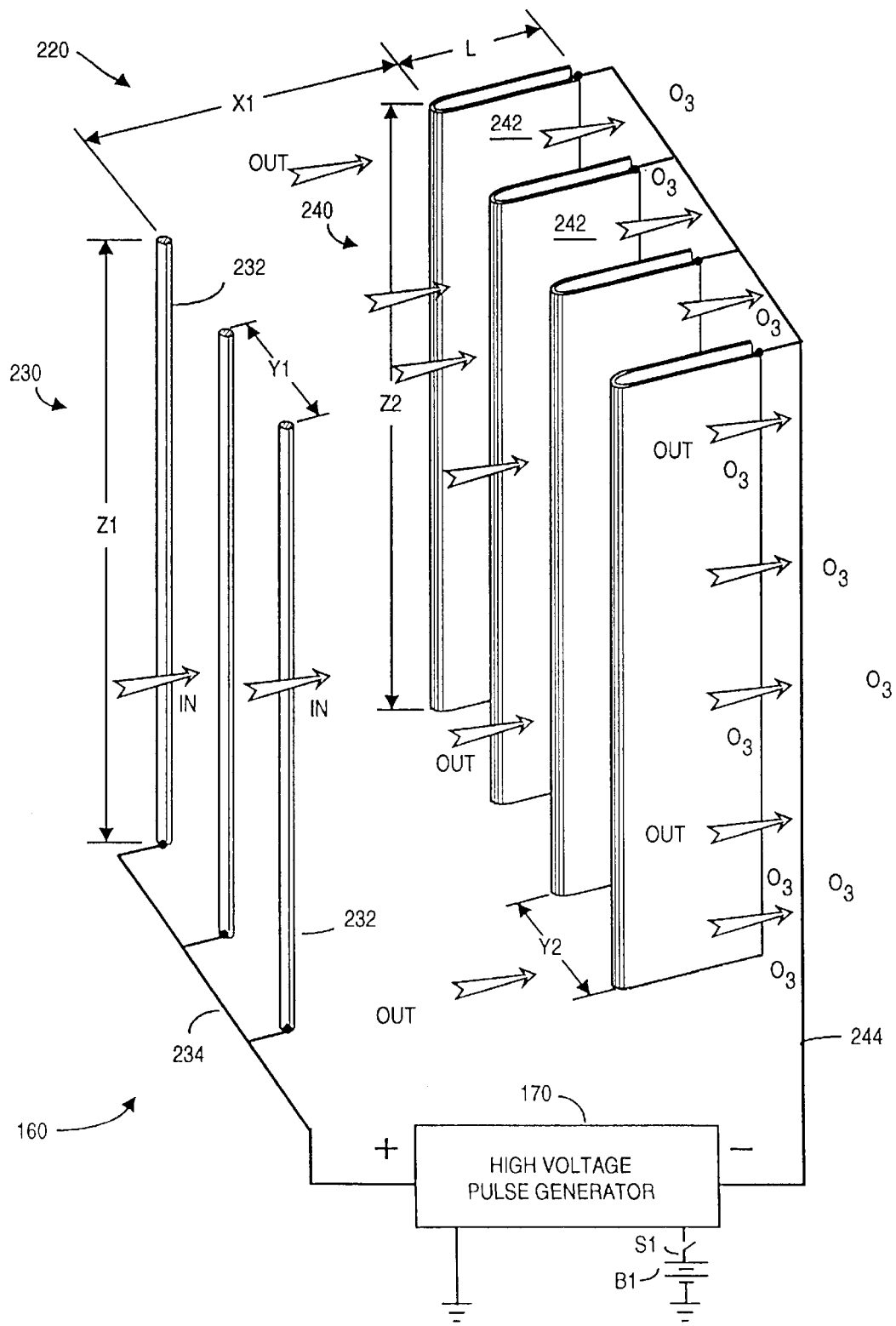
FIG. 4A is a perspective block diagram showing a first embodiment for an electrode assembly, according to the present invention.
Figure 4B:
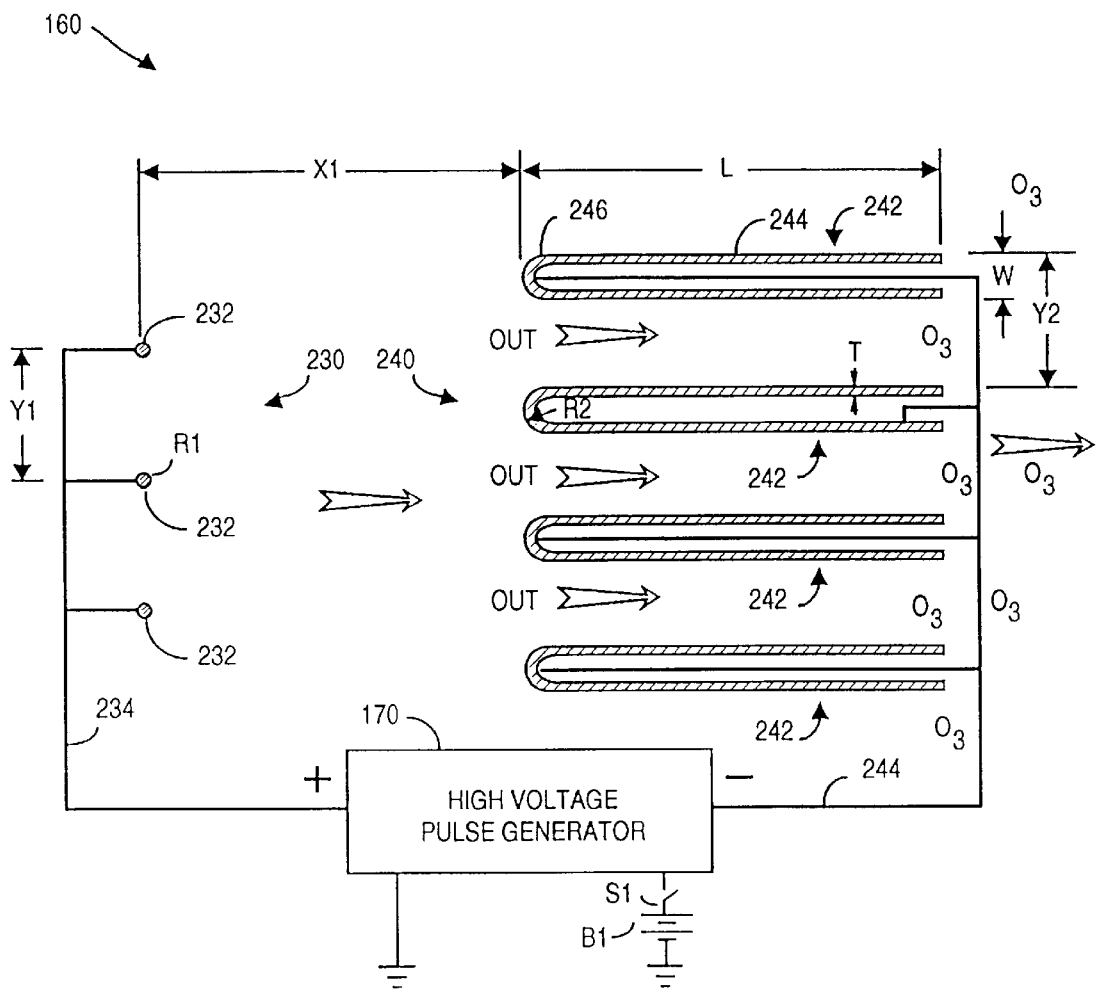
FIG. 4B is a plan block diagram of the embodiment of FIG. 4A.

Turning now to the embodiments of FIGS. 4A and 4B, electrode assembly 220 comprises a first array 230 of wire electrodes 232, and a second array 240 of generally "U"-shaped electrodes 242. In preferred embodiments, the number N1 of electrodes comprising the first array will differ by one relative to the number N2 of electrodes comprising the second array. In many of the embodiments shown, N2>N1. However, if desired, in FIG. 4A, addition first electrodes 232 could be added at the out ends of array 230 such that N1>N2, e.g., five electrodes 232 compared to four electrodes 242.

Electrodes 232 are preferably lengths of tungsten wire, whereas electrodes 242 are formed from sheet metal, preferably stainless steel, although brass or other sheet metal could be used. The sheet metal is readily formed to define side regions 244 and bulbous nose region 246 for hollow elongated "U"-shaped electrodes 242. While FIG. 4A depicts four electrodes 242 in second array 240 and three electrodes 232 in first array 230, as noted, other numbers of electrodes in each array could be used, preferably retaining a symmetrically staggered configuration as shown.

As best seen in FIG. 4B, the spaced-apart configuration between the arrays is staggered such that each first array electrode 232 is substantially equidistant from two second array electrodes 242. This symmetrical staggering has been found to be an especially efficient electrode placement. Preferably the staggering geometry is symmetrical in that adjacent electrodes 232 or adjacent electrodes 242 are spaced-apart a constant distance, Y1 and Y2 respectively.

However, a non-symmetrical configuration could also be used, although ion emission and air flow would likely be diminished. Also, it is understood that the number of electrodes 232 and 242 may differ from what is shown.

In FIGS. 4A, typically dimensions are as follows: diameter of electrodes 232 is about 0.08 mm, distances Y1 and Y2 are each about 16 mm, distance X1 is about 16 mm, distance L is about 20 mm, and electrode heights Z1 and Z2 are each about 100 mm. The width W of electrodes 242 is preferably about 4 mm, and the thickness of the material from which electrodes 242 are formed is about 0.5 mm. Of course other dimensions and shapes could be used. It is preferred that electrodes 232 be small in diameter to help establish a desired high voltage field. On the other hand, it is desired that electrodes 232 (as well as electrodes 242) be sufficiently robust to withstand occasional cleaning.

Electrodes 232 in first array 230 are coupled by a conductor 234 to a first (preferably positive) output port of high voltage pulse generator 170, and electrodes 242 in second array 240 are coupled by a conductor 244 to a second (preferably negative) output port of generator 170. It is relatively unimportant where on the various electrodes electrical connection is made to conductors 234 or 244. Thus, by way of example FIG. 4B depicts conductor 244 making connection with some electrodes 242 internal to bulbous end 246, while other electrodes 242 make electrical connection to conductor 244 elsewhere on the electrode. Electrical connection to the various electrodes 242 could also be made on the electrode external surface providing no substantial impairment of the outflow airstream results.

The ratio of the effective electric field emanating area of electrode 232 to the nearest effective area of electrodes 242 is at least about 15:1, and preferably is at least 20:1. Beyond a ratio of say 35:1, little or no performance improvement results. Thus, in the embodiment of FIG. 4A and FIG. 4B, the ratio R2/R1 2 mm/0.08 mm 25:1.

In this and the other embodiments to be described herein, ionization appears to occur at the smaller electrode(s) 232 in the first electrode array 230, with ozone production occurring as a function of high voltage arcing. For example, increasing the peak-to-peak voltage amplitude and/or duty cycle of the pulses from the high voltage pulse generator 170 can increase ozone content in the output flow of ionized air.

Figure 4C:
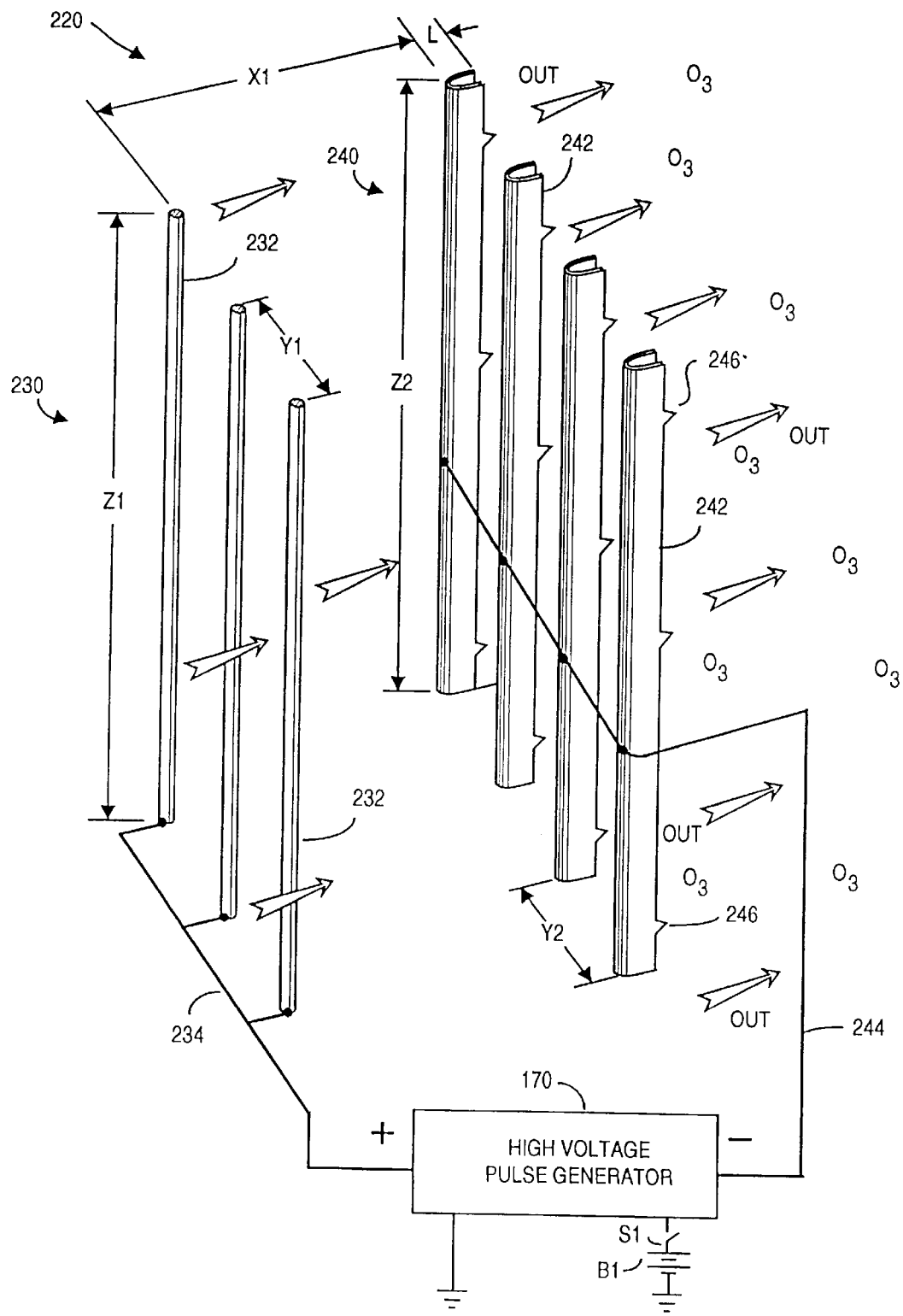
FIG. 4C is a perspective block diagram showing a second embodiment for an electrode assembly, according to the present invention.
Figure 4D:
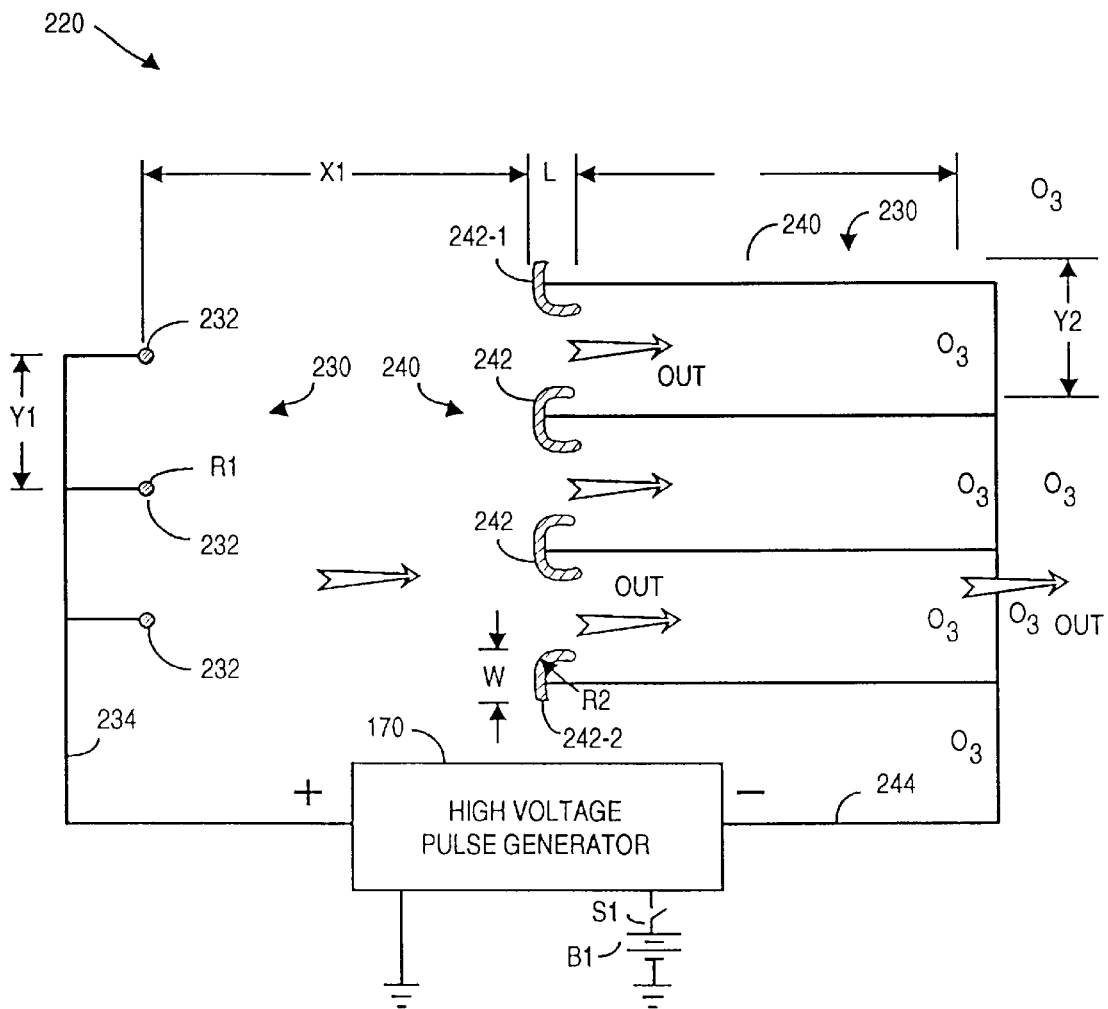
FIG. 4D is a plan block diagram of a modified version of the embodiment of FIG. 4C.

In the Embodiment of FIGS. 4A and 4C, each "U"-shaped electrode 242 has two trailing edges 244 that promote efficient kinetic transport of the outflow of ionized air and $O_3$. By contrast, the embodiments of FIGS. 4C and 4D depict somewhat truncated versions of electrodes 242. Whereas dimension L in the embodiment of FIGS. 4A and 4B was about 20 mm, in FIGS. 4C and 4D, L has been shortened to about: 8 mm. Other dimensions in FIG. 4C preferably are similar to those stated for FIGS. 4A and 4B. In FIGS. 4C and 4D, the inclusion of point-like regions 246 on the trailing edge of electrodes 242 seems to promote more efficient generation of ionized air flow. It will be appreciated that the configuration of second electrode array 240 in FIG. 4C can be more robust than the configuration of FIGS. 4A and 4B, by virtue of the shorter trailing edge geometry. As noted earlier, a symmetrical staggered geometry for the first and second electrode arrays is preferred for the configuration of FIG. 4C.

In the (embodiment of FIG. 4D, the outermost second electrodes, denoted 242-1 and 242-2, have substantially no outermost trailing edges. Dimension L in FIG. 4D is preferably about 3 mm, and other dimensions may be as stated for the configuration of FIGS. 4A and 4B. Again, the R2/R1 ratio for the embodiment of FIG. 4D preferably exceeds about 20:1.

Figure 4E:
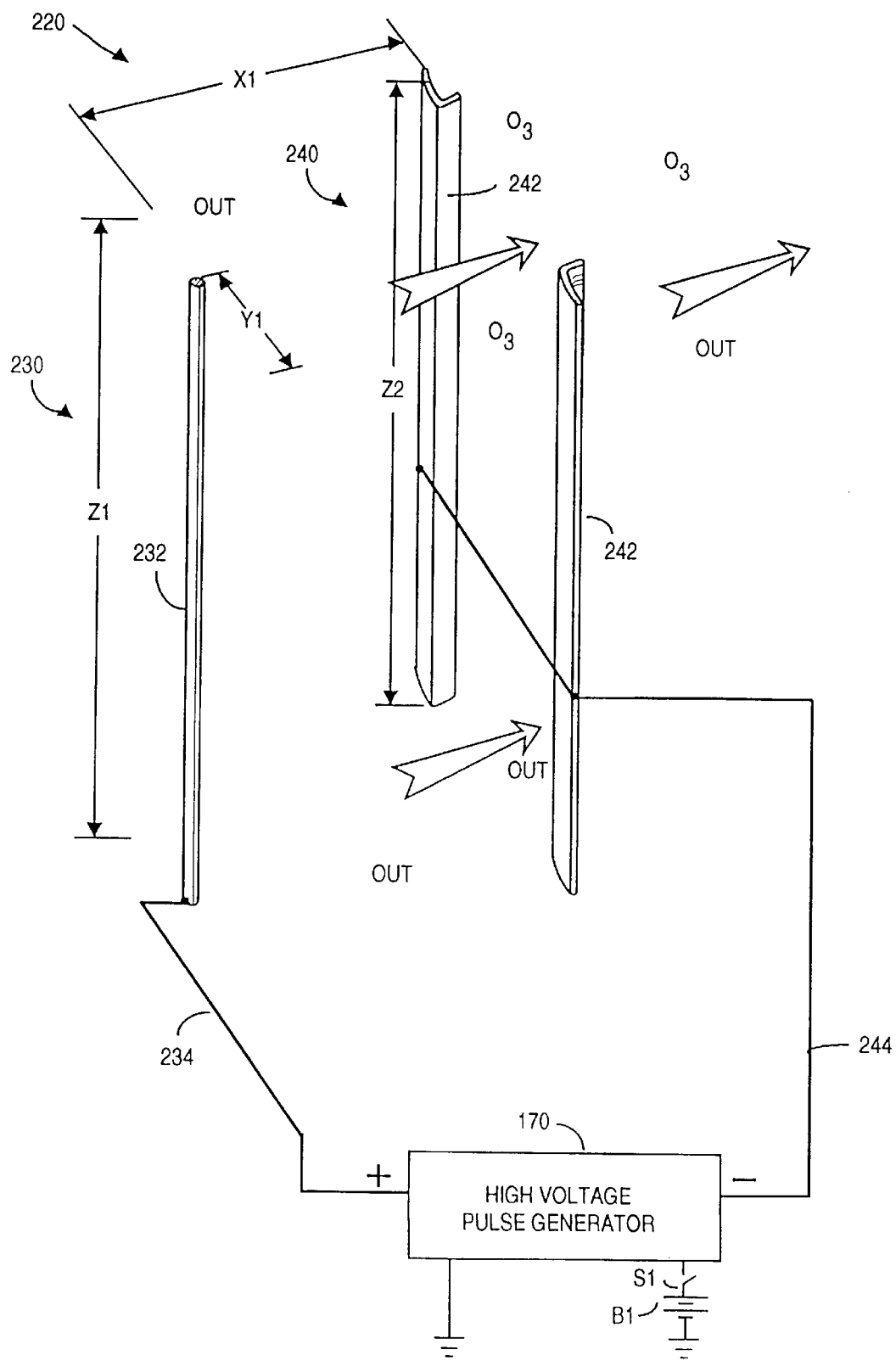
FIG. 4E is a perspective block diagram showing a third embodiment for an electrode assembly, according to the present invention.
Figure 4F:
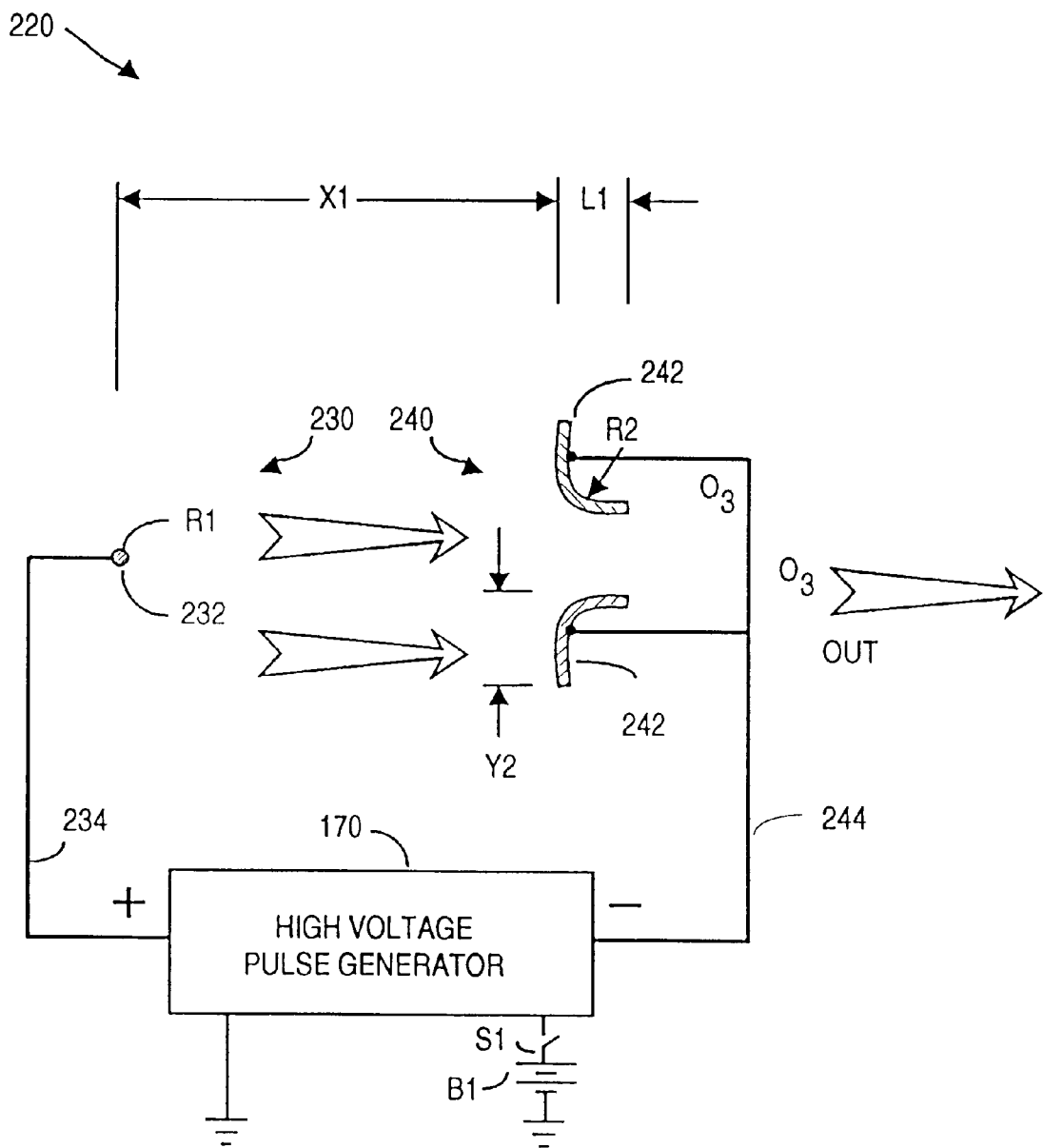
FIG. 4F is a plan block diagram of the embodiment of FIG. 4E.

FIGS. 4E and 4F depict another embodiment of electrode assembly 220, in which the first electrode array comprises a single wire electrode 232, and the second electrode array comprises a single pair of curved "L"-shaped electrodes 242, in cross-section. Typical dimensions, where different than what has been stated for earlier-described embodiments, are X1≈12 mm, Y1≈6 mm, Y2≈3 mm, and L1≈3 mm. The effective R2/R1 ratio is again greater than about 20:1. The fewer electrodes comprising assembly 220 in FIGS. 4E and 4F promote economy of construction, and ease of cleaning, although more than one electrode 232, and more than two electrodes 242 could of course be employed. This embodiment again incorporates the staggered symmetry described earlier, in which electrode 232 is equidistant from two electrodes 242.

Figure 4G:
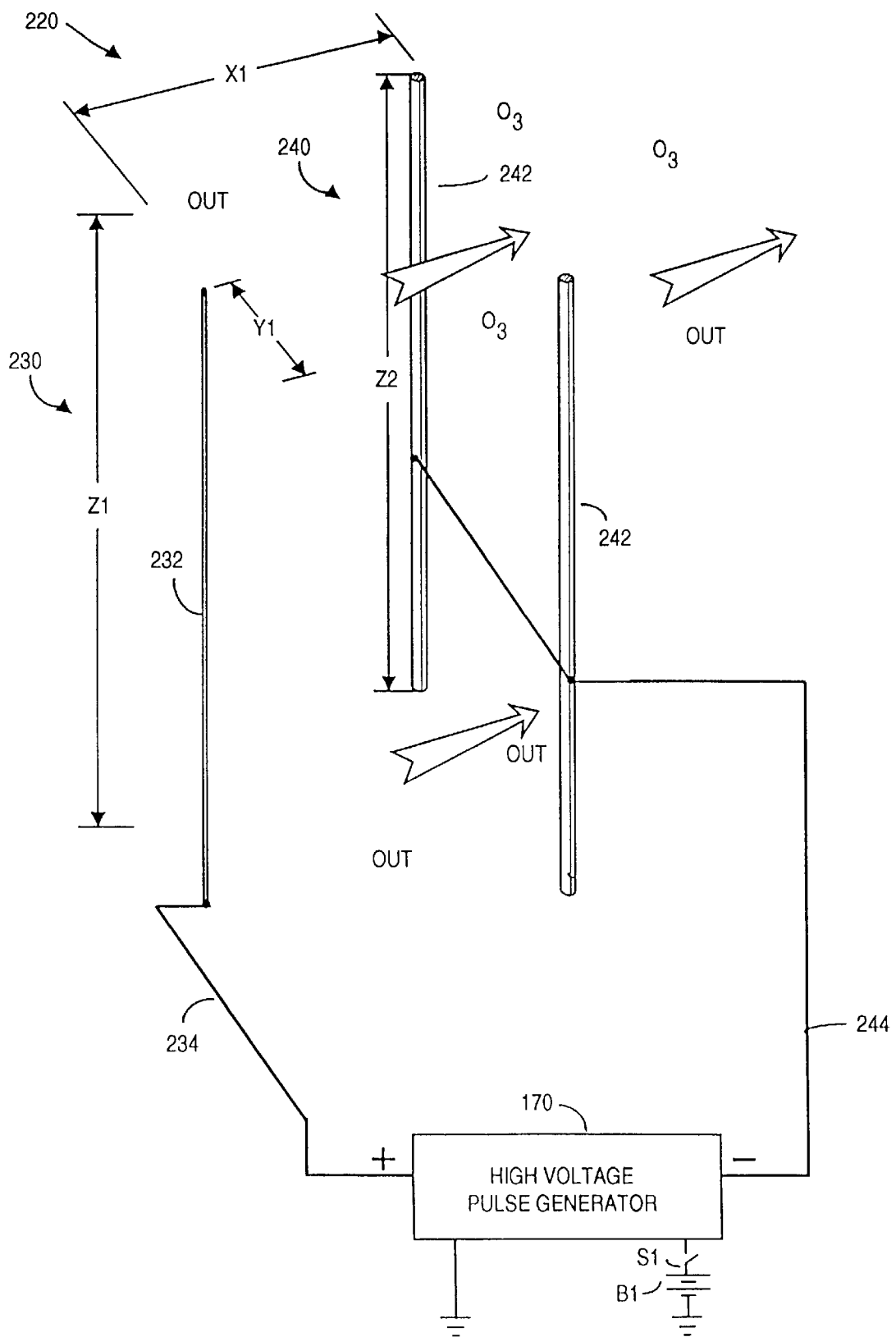
FIG. 4G is a perspective block diagram showing a fourth embodiment for an electrode assembly, according to the present invention.
Figure 4H:
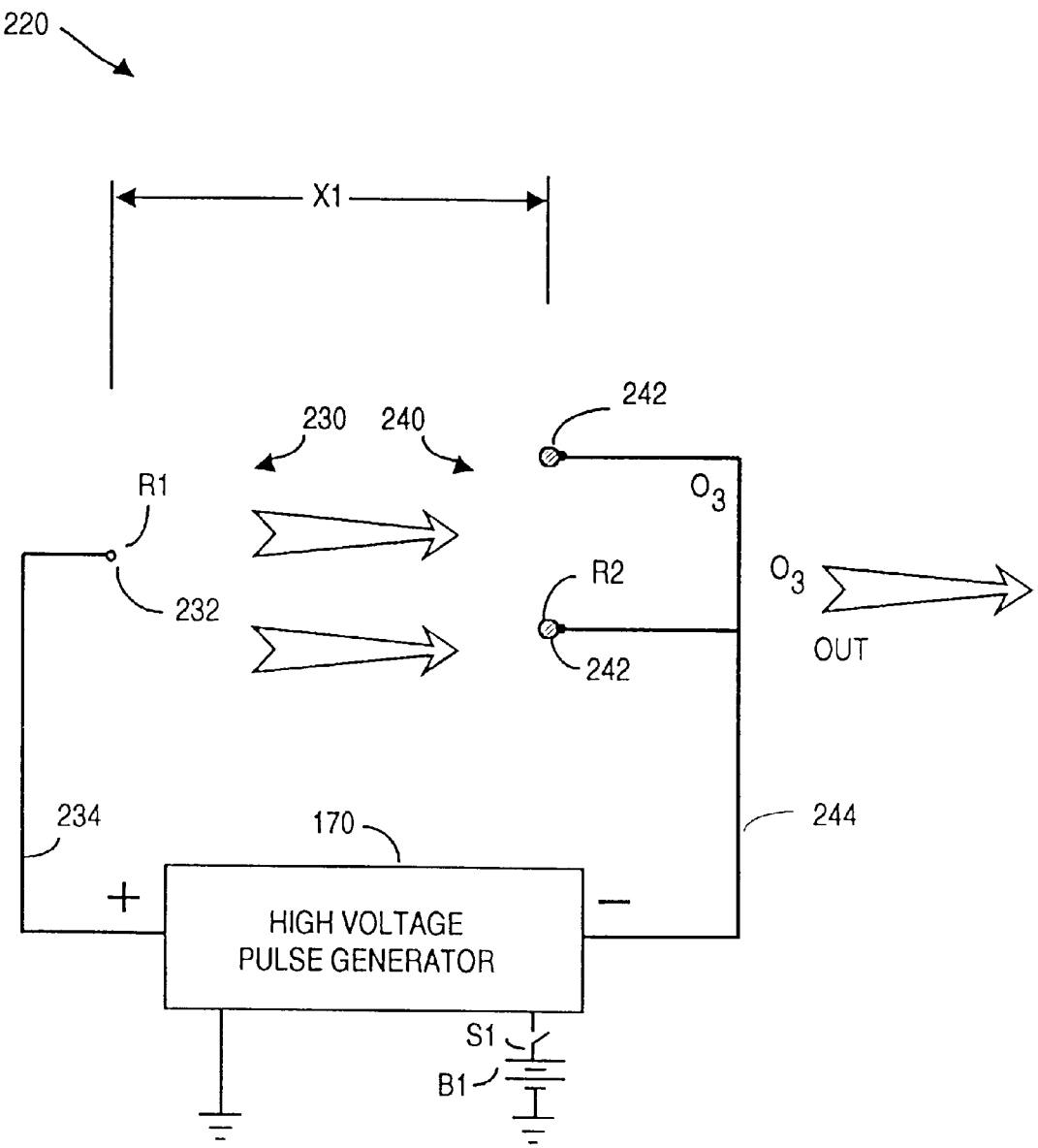
FIG. 4H is a plan block diagram of the embodiment of FIG. 4G.

FIGS. 4G and 4H shown yet another embodiment for electrode assembly 220. In this embodiment, first electrode array 230 is a length of wire 232, while the second electrode array 240 comprises a pair of rod or columnar electrodes 242. As in embodiments described earlier herein, it is preferred that electrode 232 be symmetrically equidistant from electrodes 242. Wire electrode 232 is preferably perhaps 0.08 mm tungsten, whereas columnar electrodes 242 are perhaps 2 mm diameter stainless steel. Thus, in this embodiment the R2/R1 ratio is about 25:1. Other dimensions may be similar to other configurations, e.g., FIGS. 4E, 4F. Of course electrode assembly 220 may comprise more than one electrode 232, and more than two electrodes 242.

Figure 4I:
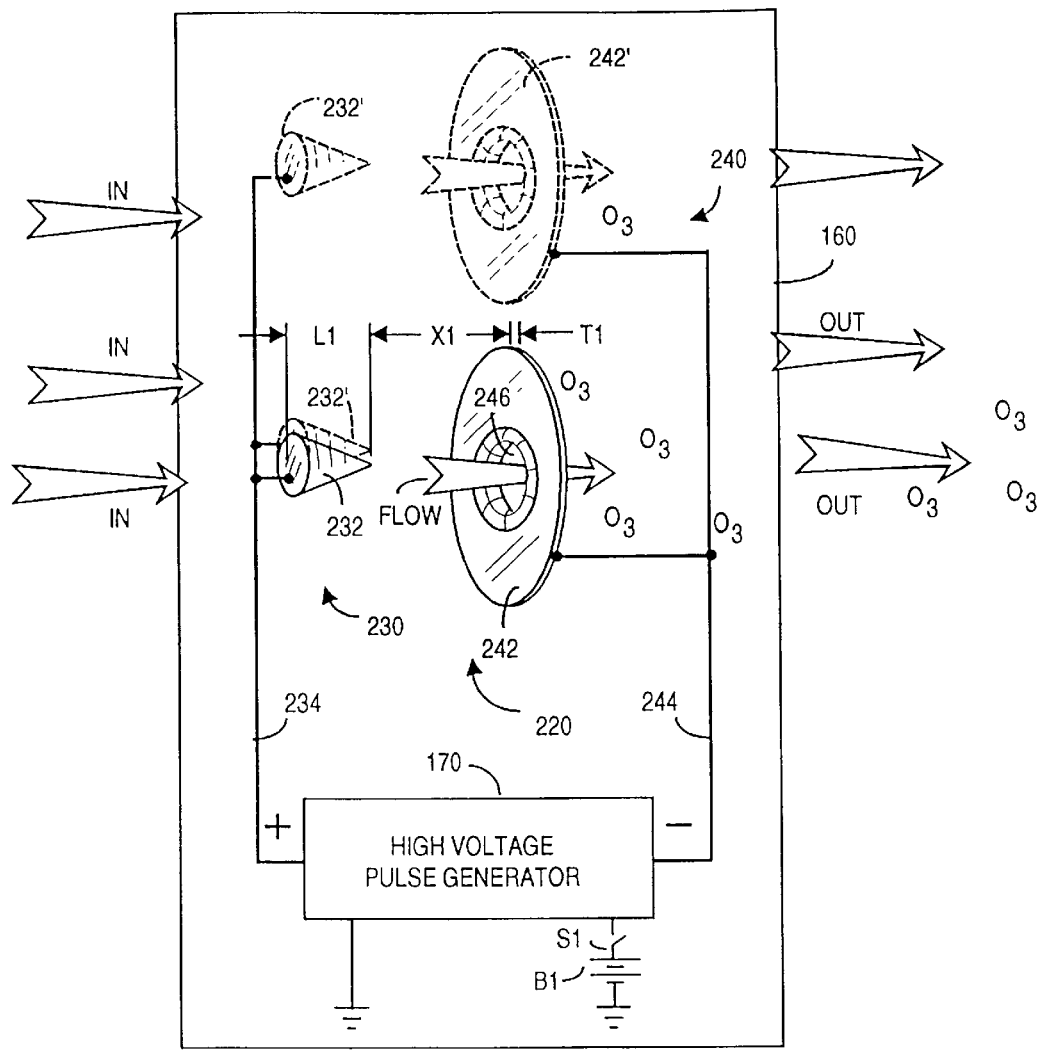
FIG. 4I is a perspective block diagram showing a fifth embodiment for an electrode assembly, according to the present invention.
Figure 4J:
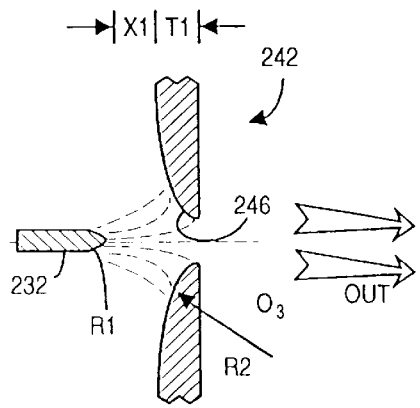
FIG. 4J is a detailed cross-sectional view of a portion of the embodiment of FIG. 4I.

An especially preferred embodiment is shown in FIG. 4I and FIG. 4J. In these figures, the first electrode assembly comprises a single pin-like element 232 disposed coaxially with a second electrode array that comprises a single ring-like electrode 242 having a rounded inner opening 246. However, as indicated by phantom elements 232', 242', electrode assembly 220 may comprise a plurality of such pin-like and ring-like elements. Preferably electrode 232 is tungsten, and electrode 242 is stainless steel.

Typical dimensions for the embodiment of FIG. 4I and FIG. 4J are L1≈10 mm, X1≈9.5 mm, T1≈0.5 mm, and the diameter of opening 246 is about 12 mm. Dimension L1 preferably is sufficiently long that upstream portions of electrode 232 (e.g., portions to the left in FIG. 4I) do not interfere with the electrical field between electrode 232 and the collector electrode 242. However, as shown in FIG. 4J, the effect R2/R1 ratio is governed by the tip geometry of electrode 232. Again, in the preferred embodiment, this ratio exceeds about 20:1. Lines drawn in phantom in FIG. 4J depict theoretical electric force field lines, emanating from emitter electrode 232, and terminating on the curved surface of collector electrode 246. Preferably the bulk of the field emanates within about ±45° of coaxial axis between electrode 232 and electrode 242. On the other hand, if the opening in electrode 242 and/or electrode 232 and 242 geometry is such that too narrow an angle about the coaxial axis exists, air flow will be unduly restricted.

One advantage of the ring-pin electrode assembly configuration shown in FIG. 4I is that the flat regions of ring-like electrode 242 provide sufficient surface area to which dust entrained in the moving air stream can attach, yet be readily cleaned. As a result, the air stream (OUT) emitted by the hair brush has reduced dust especially contrasted to prior art kinetic air mover configurations.

Further, the ring-pin configuration advantageously generates more ozone than prior art configurations, or the configurations of FIGS. 4A–4H. For example, whereas the configurations of FIGS. 4A–4H may generate perhaps 50 ppb ozone, the configuration of FIG. 4I can generate about 2,000 ppb ozone, without an increase in demand upon power supply B1.

Figure 4K:
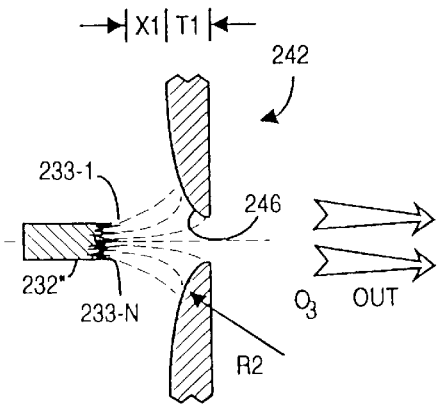
FIG. 4K is a detailed cross-sectional view of a portion of an alternative to the embodiment of FIG. 4I.

Nonetheless it will be appreciated that applicants' first array pin electrodes may be utilized with the second array electrodes of FIGS. 4A–4H. Further, applicants' second array ring electrodes may be utilized with the first array electrodes of FIGS. 4A–4H. For example, in modifications of the embodiments of FIGS. 4A–4H, each wire or columnar electrode 232 is replaced by a column of electrically series-connected pin electrodes (e.g., as shown in FIGS. 4I–4K), while retaining the second electrode arrays as depicted in these figures. By the same token, in other modifications of the embodiments of FIGS. 4A–4H, the first array electrodes can remain as depicted, but each of the second array electrodes 242 is replaced by a column of electrically series-connected ring electrodes (e.g., as shown in FIGS. 4I–4K).

In FIG. 4J, a detailed cross-sectional view of the central portion of electrode 242 in FIG. 4I is shown. As best seen in FIG. 4J, curved region 246 adjacent the central opening in electrode 242 appears to provide an acceptably large surface area to which many ionization paths from the distal tip of electrode 232 have substantially equal path length. Thus, while the distal tip (or emitting tip) of electrode 232 is advantageously small to concentrate the electric field between the electrode arrays, the adjacent regions of electrode 242 preferably provide many equidistant inter-electrode array paths. A high exit flowrate of perhaps 90 feet/minute and 2,000 ppb range ozone emission attainable with this configuration confirm a high operating efficiency.

In FIG. 4K, one or more electrodes 232 is replaced by a conductive block 232" of carbon fibers, the block having a distal surface in which projecting fibers 233-1, . . . 233-N take on the appearance of a "bed of nails". The projecting fibers can each act as an emitting electrode and provide a plurality of emitting surfaces. Over a period of time, some or all of the electrodes will literally be consumed, whereupon graphite block 232" will be replaced. Materials other than graphite may be used for block 232" providing the material has a surface with projecting conductive fibers such as 233-N.

Figure 5:
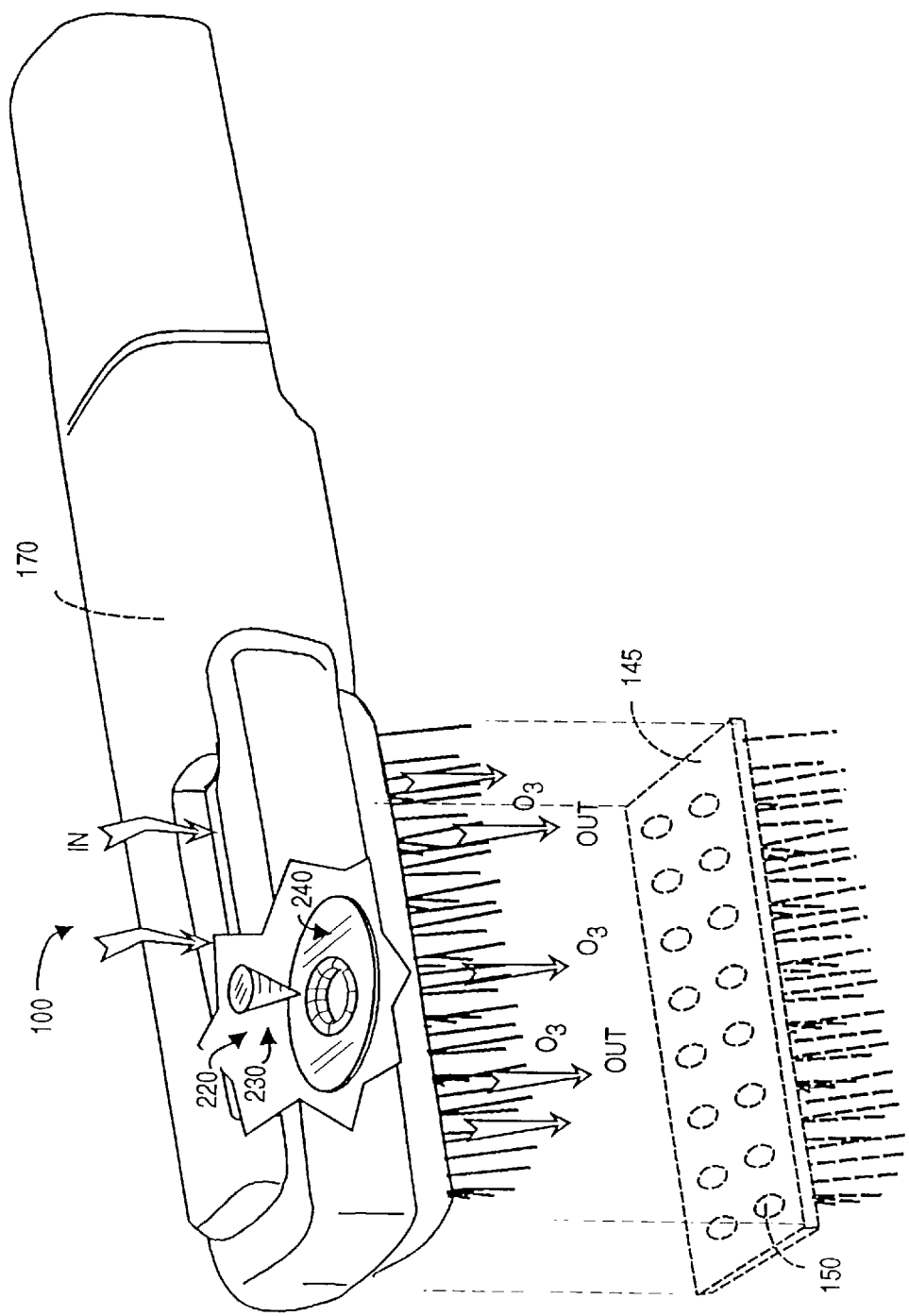
FIG. 5 is a cutaway perspective view of the present invention showing location of the electrode assembly, according to the present invention.

FIG. 5 depicts the location of a typical electrode assembly 220 within the head portion of hair brush 100, such that second electrode array 240 is closer to the brushing surface of the hair brush than is first electrode array 230. While FIG. 5 depicts an electrode assembly 220 using the ring-pin configuration of FIG. 4I, it is understood that any of the alternative configurations of FIGS. 4A–4G could instead be contained within hair brush 100. FIG. 5 also depicts the optionally removable nature of bristle block 145, and a different configuration of exit vents 150.

Preferably the inner portion of the head region of brush 100 includes an electrostatic shield that reduces detectable electromagnetic radiation outside of the brush. For example, a metal shield could be disposed within the housing, or portions of the interior of the housing could be coated with a metallic paint to reduce such radiation.

It will also be appreciated that the net output of ions could be influenced by placing a bias element near some or all of the output vents. For example, such an element could be electrically biased to neutralize negative ions, thereby increasing the net output of positive ions. It will also be appreciated that the present invention could be adjusted to produce ions without producing ozone, if desired.

Modifications and variations may be made to the disclosed embodiments without departing from the subject and spirit of the invention as defined by the following claims.

What is claimed is:

1. A self-contained ion emitting brush, comprising:
a handholdable body defining at least one vent and having a region to which a grooming attachment may be affixed;
a self-contained ion generator disposed in said body and including:
a high voltage generator having first and second output ports, one of which ports may be at a same potential as ambient air, that outputs a signal whose duty cycle can be about 10% to about 100%; and
an electrode assembly, effectively coupled between said output ports, comprising a first electrode array that includes at least one electrode having a pointed tip aimed generally in a downstream direction, and a second electrode array that includes at least one electrically conductive member through which there is defined at least one substantially circular opening disposed generally coaxial with and in a downstream direction from said pointed tip of said first electrode, said electrically conductive member having a first surface facing said first electrode array and, transitioning smoothly and continuously from said first surface, a second surface surrounding a periphery of said substantially circular opening to form a skirt-like region having a single continuous interior surface, said skirt-like region extending in said downstream direction;
wherein said ion generator outputs an electrostatic flow in a downstream direction toward said second electrode array, said electrostatic flow including at least one of ionized air and ozone.

2. The brush of claim 1, wherein:
said second electrode array is a loop of conductive material.

3. The brush of claim 1, wherein:
said first electrode array includes at least two electrodes that each have a pointed tip aimed generally toward said opening; and
said second electrode array is a single ring of conductive material encircling said opening.

4. The brush of claim 1, wherein:
said first electrode array includes at least two electrodes that each have a pointed tip; and
said second electrode array includes at least two electrically conductive members that each define a substantially circular opening disposed generally coaxial with and in a downstream direction from a pointed tip of an electrode in said first electrode array, each of said electrically conductive members having a first surface facing said first electrode array and, transitioning smoothly and continuously from said first surface, a second surface surrounding a periphery of said substantially circular opening to form a skirt-like region having a single continuous interior surface, said skirt-like region extending in said downstream direction.

5. The brush of claim 1, wherein:
said first electrode array includes at least one electrode made from a material having a distal end that defines a plurality of projecting conductive fibers.

6. The brush of claim 1, wherein an edge of said electrically conductive member surrounding said opening is rounded on a member surface facing said first electrode array.

7. The brush of claim 1, wherein said high voltage generator provides a first potential measurable relative to ground to said first electrode array and provides a second potential measurable relative to ground to said second electrode array.

8. The brush of claim 7, wherein at least one of said first potential and said second potential has an absolute magnitude of at least about 1 kV.

9. The brush of claim 1, further including said grooming attachment.

10. The brush of claim 1, further including said grooming attachment, wherein said grooming attachment includes bristles.

11. The brush of claim 1, wherein said second electrode array has at least one characteristic selected from a group consisting of (a) said member defines in cross-section a tapered region terminating towards said circular opening, (b) said member defines in cross-section a rounded region terminating towards said circular opening, (c) said member defines in cross-section a rounded profile terminating in said circular opening, (d) a ratio of effective radius of a first electrode array-facing edge of said member surrounding said opening to effective radius of said pointed tip exceeds about 15:1, and (e) said member includes stainless steel.

12. The brush of claim 1, wherein said electrode in said first electrode array has at least one characteristic selected from a group consisting of (a) said electrode includes tungsten, (b) said electrdoe includes stainless steel, and (c) said electrode includes projecting fibers of carbon.

13. A method of providing a self-contained ion emitting brush, comprising the following steps:
(a) providing a handholdable body having a region to which a grooming attachment may be affixed;
(b) disposing within said body an electrode assembly comprising a first electrode array that includes at least one electrode having a pointed tip aimed generally in a downstream direction, and a second electrode array that includes at least one electrically conductive member through which there is defined at least one substantially circular opening disposed generally coaxial with and in a downstream direction from said pointed tip of said first electrode, said electrically conductive member formed with a first surface facing said first electrode array and, transitioning smoothly and continuously from said first surface, and formed with a second surface surrounding a periphery of said of said substantially circular opening to form a skirt-like region having a sinle continuous interior surface, said skirt-like region extending in said donwstream direction; and
(c) within said body, generating high voltage with a duty cycle that can be about 10% to about 100% and coupling said high voltage across said first electrode array and said second electrode array;
wherein an electrostatic flow in a downstream direction toward said second electrode array is created, said electrostatic flow including at least one of ionized air and ozone.

14. The method of claim 13, wherein step (b) includes providing said second electrode array as a loop of conductive material.

15. The method of claim 13, wherein step (b) includes providing said first electrode array with at least two electrodes that each have a pointed tip aimed generally toward said opening; and providing said second electrode array as a single ring of conductive material encircling said opening.

16. The method of claim 13, wherein step (b) includes:
providing said first electrode array with at least first and second electrodes that each have a pointed tip; and
providing said second electrode array with at least first and second electrically conductive members thateach define a substantially circular opening, and disposing said first and second electrically conductive members generally coaxial with and in a downstream direction from, respectively, said pointed tip said first and second electrodes in said first electrode array, each of said electrically conductive members formed with a first surface facing said first electrode array and, transitioning smoothly and continuously from said first surface, and formed with a second surface surrounding a periphery of said substantially circular opening to form a skirt-like region having a single continuous interior surface, said skirt-like region extending in said downstream direction.

17. The method of claim 13, wherein step (b) includes:

providing said first electrode array with at least one electrode made from a material having a distal end that includes a plurality of projecting conductive fibers.

18. The method of claim 13, wherein step (c) includes rounding an edge of said electrically conductive member surrounding said opening on a member surface facing said first electrode array.

19. The method of claim 13, wherein step (c) includes generating and coupling said high voltage to provide a first potential measurable relative to ground to said first electrode array and to provide a second potential measurable relative to ground to said second electrode array.

20. The method of claim 13, wherein at least one of said first potential and said second potential has an absolute magnitude of at least about 1 kV.

21. A self-contained ion emitting brush, comprising:

a handholdable body defining at least one vent and having a region to which a grooming attachment may be affixed;

a self-contained ion generator disposed in said body and including:

a high voltage generator having first and second output ports, one of which ports may be at a same potential as ambient air, that outputs a signal whose duty cycle can be about 10% to about 100%; and an electrode assembly, effectively coupled between said output ports, comprising a first electrode array that includes at least one wire electrode, and a second electrode array that includes at least two electrically conductive members that are disposed parallel to said wire electrode and are equidistant thererfrom;

wherein said ion generator outputs an electrostatic flow in a downstream direction toward said second electrode array, said electrostatic flow including at least one of ionized air and ozone.

22. The brush of claim 21, wherein said electrically conductive members in said second electrode array include at least two electrically conductive electrodes that in cross-section define a "U"-shape having a bulbous nose region and first and second trailing edge regions and are disposed with said bulbous nose regions facing said wire electrode and being equidistant therefrom.

23. The brush of claim 21, wherein an electrode in said second electrode array has at least one characteristic selected from a group consisting of (a) a portion of one trailing edge region is longer than a remaining trailing edge region on said electrode, (b) said trailing edge region defines at least one pointed projection facing downstream, and (c) a ratio of effective radius of an electrode in said second electrode array to effective radius of said wire electrode exceeds about 15:1.

24. The brush of claim 21, wherein:

said second electrode array includes at least two electrically conductive electrodes that in cross-section definean "L"-shaped having a curved nose region;

the "L"-shaped electrodes being disposed such that said curved nose regions face said wire electrode and are equidistant therefrom.

25. The brush of claim 21, wherein:

said second electrode array includes at least first and second conductive electrodes disposed parallel to said wire electrode and equidistant therefrom, the first conductive electrode having a side surface parallel to a side surface of the second conductive electrode.

26. The brush of claim 25, wherein a ratio of said first conductive electrode to radius of said wire electrode exceeds about 15:1.

27. The brush of claim 21, wherein a portion of electrodes in said second array include at least one pointed projection facing downstream.

28. A method of providing a self-contained ion emitting brush, comprising the following steps:

(a) providing a handholdable body having a region to which a grooming attachment may be affixed;

(b) disposing within said body an electrode assembly comprising a first electrode array including a wire electrode, and a second electrode array including at least two electrically conductive members disposed parallel to said wire electrode and equidistant therefrom; and (c) within said body, generating high voltage with a duty cycle that can be about 10% to about 100% and coupling said high voltage across said first electrode array and said second elecrode array;

wherein an electrostatic flow is created that flows downstream toward second electrode array, said electrostatic flow including at least one of ionized air and ozone.

29. The method of claim 28, wherein steo (b) includes providing said electrically conductive members in said second electrode array with at least two electrically conductive electrodes that in cross station define a "U"-shape having a bulbous nose region and first and second trailing edge regions and are disposed with said bulbous nose regions facing said wire electrode and being equidistant therefrom.

30. The method of claim 28, wherein step (b) includes providing said second electrode array with at least two electrically conductive electrodes that in a cross-section define "L"-shape having a curved nose region and are disposed such that said curved nose regions face said wire electrode and are equidistant therefrom.

31. The method of claim 27, wherein an edge portion of said electrically conductive members in said second electrode array include at least one pointed projection facing downstream.

32. The method of claim 28, wherein an edge portion of said electrically conductive members in said second electrode array include at least one pointed projection facing downstream.

* * * * *